(12) United States Patent
Barnes et al.

(10) Patent No.: US 11,879,831 B2
(45) Date of Patent: *Jan. 23, 2024

(54) METHOD FOR MEASURING WET FRICTION OF HAIR

(71) Applicant: Conopco, Inc., Englewood Cliffs, NJ (US)

(72) Inventors: Andrew Anthony Howard Barnes, Port Sunlight (GB); Fraser Ian Bell, Higher Bebington (GB); Colin Christopher David Giles, Oxton (GB); Sophia Paraskevi Clare Moghadam, Bromborough (GB); Rongrong Zhou, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 1080 days.

This patent is subject to a terminal disclaimer.

(21) Appl. No.: 16/497,441

(22) PCT Filed: Mar. 21, 2018

(86) PCT No.: PCT/EP2018/057210
§ 371 (c)(1),
(2) Date: Sep. 24, 2019

(87) PCT Pub. No.: WO2018/177850
PCT Pub. Date: Oct. 4, 2018

(65) Prior Publication Data
US 2021/0041349 A1   Feb. 11, 2021

(30) Foreign Application Priority Data

Mar. 29, 2017 (EP) .................. 17163626

(51) Int. Cl.
*G01N 19/02* (2006.01)
*A61K 8/41* (2006.01)
*A61Q 5/12* (2006.01)

(52) U.S. Cl.
CPC ............. *G01N 19/02* (2013.01); *A61K 8/416* (2013.01); *A61Q 5/12* (2013.01)

(58) Field of Classification Search
CPC . G01N 19/02; A61Q 5/12; A61Q 5/02; A61Q 5/00
See application file for complete search history.

(56) References Cited

U.S. PATENT DOCUMENTS

| 2,712,235 A | 7/1955 | Harlan |
| 3,161,704 A | 12/1964 | Le Grand |

(Continued)

FOREIGN PATENT DOCUMENTS

| CN | 2569129 | 8/2003 |
| CN | 101772698 | 7/2010 |

(Continued)

OTHER PUBLICATIONS

Bharat et al.; Friction and wear studies of human hair and skin; Wear; 2005; 1012-1021; XP002774198; vol. 259.

(Continued)

*Primary Examiner* — Timothy P Thomas
(74) *Attorney, Agent, or Firm* — Gerard J. McGowan, Jr.

(57) ABSTRACT

A method of measuring a wet friction of a bundle of hair, using a system which includes a friction probe having a contact surface and fitted with a weight in the range of from 10 g to 500 g, inclusive, a means for securing the bundle of hair, and a water bath, the friction probe being connected to a texture analyser, the method including the step of i) providing a bundle of hair fibres. The method also includes the steps of ii) aligning the bundle of hair fibres; iii) securing (Continued)

the bundle of hair fibres; iv) immersing the bundle of hair fibres under water in the water bath; v) contacting the bundle of hair fibres with the contact surface of the friction probe, which is fitted with the weight; vi) moving the probe along the hair fibres; and vii) recording the friction generated under step vi).

7 Claims, 2 Drawing Sheets

(56) References Cited

U.S. PATENT DOCUMENTS

| | | | |
|---|---|---|---|
| 3,717,025 | A | 2/1973 | Kronenberg |
| 3,721,250 | A | 3/1973 | Walter |
| 3,921,443 | A | 11/1975 | Yates |
| 3,946,606 | A | 3/1976 | Abrioux et al. |
| 3,960,160 | A | 6/1976 | Hogan |
| 4,061,022 | A | 6/1977 | Yates |
| 4,167,869 | A | 9/1979 | Gikas |
| 4,286,469 | A | 9/1981 | Trias |
| 4,722,218 | A | 2/1988 | Strader |
| 5,358,667 | A | 10/1994 | Bergmann |
| 5,373,723 | A | 12/1994 | Chou |
| 5,767,104 | A | 6/1998 | Bar-Shalom |
| 6,234,003 | B1 | 5/2001 | Nakajima |
| 6,321,586 | B1 | 11/2001 | Wojtowicz |
| 6,494,076 | B1 | 12/2002 | Gent |
| 6,817,222 | B2 | 11/2004 | Day et al. |
| 7,691,398 | B2 | 6/2010 | Arai et al. |
| 8,833,137 | B2 | 9/2014 | Yagnik et al. |
| 9,823,180 | B2 | 11/2017 | Amano |
| 9,829,419 | B2 | 11/2017 | Fawcett |
| 10,024,841 | B2 | 7/2018 | Meinert |
| 10,151,684 | B2 | 12/2018 | Ganguli |
| 10,809,181 | B2 | 10/2020 | Justynska-Reimann |
| 2003/0140707 | A1 | 7/2003 | Pyle et al. |
| 2003/0233861 | A1 | 12/2003 | Woolston et al. |
| 2005/0112074 | A1* | 5/2005 | Arai .................. A61Q 5/10 424/401 |
| 2006/0184068 | A1 | 8/2006 | Shibuichi et al. |
| 2007/0288186 | A1* | 12/2007 | Datta .................. G01N 19/02 702/81 |
| 2008/0233069 | A1 | 9/2008 | Tamareselvy |
| 2009/0031791 | A1 | 2/2009 | Zahouani |
| 2009/0071228 | A1 | 3/2009 | Sherman et al. |
| 2009/0188330 | A1 | 7/2009 | Kindersley |
| 2009/0324529 | A1 | 12/2009 | Okada et al. |
| 2009/0324532 | A1 | 12/2009 | Okada et al. |
| 2010/0223977 | A1 | 9/2010 | Debon |
| 2010/0229625 | A1 | 9/2010 | Debon et al. |
| 2012/0222466 | A1 | 9/2012 | Bailey et al. |
| 2013/0067986 | A1 | 3/2013 | Girdler et al. |
| 2014/0311210 | A1 | 10/2014 | Rounds |
| 2015/0093347 | A1 | 4/2015 | Uehara et al. |
| 2015/0241332 | A1 | 8/2015 | Amano |
| 2015/0292989 | A1 | 10/2015 | Regimand et al. |
| 2015/0355063 | A1 | 12/2015 | Fawcett et al. |
| 2016/0061809 | A1 | 3/2016 | Meinert et al. |
| 2016/0279048 | A1 | 9/2016 | Jayaswal |
| 2017/0138839 | A1 | 5/2017 | Ganguli |
| 2017/0231897 | A1 | 8/2017 | Avery |
| 2017/0266099 | A1 | 9/2017 | Kroon |
| 2018/0177696 | A1 | 6/2018 | Schrott |
| 2018/0221266 | A1 | 8/2018 | Zhao |
| 2018/0345048 | A1 | 12/2018 | Dussaud |
| 2018/0353396 | A1 | 12/2018 | Paul |
| 2018/0353398 | A1 | 12/2018 | Torres Rivera et al. |
| 2019/0192405 | A1 | 6/2019 | Zhao et al. |
| 2019/0293548 | A1 | 9/2019 | Krishan |
| 2020/0197273 | A1 | 6/2020 | Coan |
| 2020/0217779 | A1 | 7/2020 | Brada |
| 2020/0330351 | A1 | 10/2020 | Kong |

FOREIGN PATENT DOCUMENTS

| | | |
|---|---|---|
| CN | 102175600 | 9/2011 |
| CN | 102216754 | 10/2011 |
| EP | 0965834 | 12/1999 |
| EP | 1652555 | 5/2006 |
| EP | 3287119 | 2/2018 |
| GB | 1157644 | 7/1969 |
| JP | 57166545 | 10/1982 |
| JP | 62273433 | 11/1987 |
| JP | 2005515989 | 2/2005 |
| JP | 2005315594 | 11/2005 |
| JP | 2016531873 | 10/2016 |
| WO | WO9115763 | 10/1991 |
| WO | WO0224071 | 3/2002 |
| WO | WO2014016351 | 1/2014 |
| WO | WO2014016352 | 1/2014 |
| WO | WO2014016354 | 1/2014 |
| WO | WO2014016353 | 3/2014 |
| WO | WO2015043931 | 2/2015 |

OTHER PUBLICATIONS

Search Report and Written Opinion in PCTEP2018057202; dated May 30, 2018.

Search Report and Written Opinion in EP17163597; dated Jan. 12, 2018.

Search Report and Written Opinion in EP17163626; dated Oct. 9, 2017.

Clarence R. Robbins; Chemical and physical behavior of human; Chemical and physical behavior of human; pp. 439-441; United States of America.

Aita et al.; Friction and Surface Temperature of Wet Hair Containing Water, Oil, or Oil-in-Water Emulsion; Journal of Oleo Science; Jan. 22, 2016; pp. 493-498; No. 65(6); Japan Oil Chemists Society.

Jachowicz et al.; "Using Texture Analysis to Substantiate Hair Care Claims"; Cosmetics & Toiletries Magazine; Sep. 2006; pp. 69-76; vol. 121, No. 9.

Newman et al.; "A Quantitative Characterization of Combing Force"; Journal of Cosmetic Science; Dec. 9, 1973; pp. 773-782; No. 24.

Clarence Robbins; "Chapter 9—The Physical Properties of Hair Fibers"; Chemical and Physical Behavior of Human Hair, 5th Edition; 2012; pp. 537-640; .; Springer-Verlag Berlin Heidelberg.

K. Abraham Vaynberg et al., "The Aqualon SL T: A Novel Device for Measuring Hair Stiffness and Lubricity", Journal of Cosmetic Science, No. 60, Mar.-Apr. 2009.

\* cited by examiner

METHOD FOR MEASURING WET FRICTION OF HAIR

CROSS-REFERENCE TO RELATED APPLICATIONS

This application claims priority to International Patent Application No. PCT/EP2018/057210, filed on Mar. 21, 2018, and European Patent Application No. 17163626.9, filed on Mar. 29, 2017, both of which are incorporated herein by reference in their entireties.

TECHNICAL FIELD

The present disclosure relates to a method for measuring friction of wet hair, particularly relating to hair that has been treated with a hair treatment composition and to comparisons between friction of hair treated with different treatments.

BACKGROUND

Evaluation of the friction of hair provides information about the condition of the hair, which can be affected by such things as the degree of cuticle lift, cuticle breakage, surface erosion and deposition of materials on the hair surface. It can also provide information about the efficacy of friction reducing treatments and materials. This in turn enables the beneficial choice of products that suit the particular condition of the hair.

There are a number of systems and methods available for such assessments.

Chemical and Physical Behavior of Human Hair, Clarence R. Robbins, 4th Ed., Springer; pp 439-440, presents a summary of known techniques under the heading "Methods for Measuring Friction on Hair Fibers", including a method attributed to Scott and Robbins that involves attaching the root end of a hair fibre to the load cell of an Instron tensile tester, weighting the tip end and partially wrapping around two mandrels. The mandrels are attached to a crosshead and as they move downward against the fibre, the frictional tension is recorded. Friction is said to vary with rubbing speed, with greater differences being demonstrated between treatments at low rubbing speeds. Simulations of combing of dry hair and of hair immersed in water are disclosed using this method.

In US 20090324529, haft friction force is measured using a Texture Analyzer (TA), where a composition is applied to 10 g of haft sample. After spreading the composition on the hair sample, and before and after rinsing in water, friction force between the hair sample and a polyurethane pad is measured using the TA.

We disclose in EP1652555 the measurement of friction using a TA and a friction probe in the form of a stainless steel cylinder; coated with rubber material. A switch of hair is mounted onto the TA, the hair fibres being aligned by combing before being secured in a flat configuration. The friction probe is placed onto the hair and a load on the friction contact of approximately 560 g is applied. The probe is moved along the hair at a speed of 10 mms$^{-1}$ to measure the friction between the probe and the hair. The method is used to assess the friction properties of hair treated with different hair conditioners.

However, these known methods lack the sensitivity to sufficiently differentiate between some treatments. We have found that known methods do not predict the consumer differentiation of products, particularly during the rinse stage.

We have now found that measurement of friction of a bundle of hair under water, that utilizes a friction probe fitted with a weight, a securing means, and a water bath connected to a texture analyser, where the probe is moved along the hair fibres repeatedly, until a constant value is obtained, enables a surprisingly accurate measurement.

SUMMARY

In a first aspect there is provided a method of measuring wet friction of hair, using a system comprising:
 i) a friction probe, having a contact surface, said probe fitted with a weight in the range of from 10 to 500 g;
 ii) a means for securing the bundle of hair; and
 iii) a water bath;
wherein the friction probe is connected to a texture analyser; said method comprising the steps of:
 i) providing a bundle of hair fibres;
 ii) aligning the hair fibres;
 iii) securing the bundle of hair fibres;
 iv) immersing the bundle of hair fibres under water in the water bath;
 v) contacting the hair fibres with the contact surface of the friction probe, which is fitted with the weight;
 vi) moving the probe along the hair fibres; and
 vii) recording the friction generated under step vi);
 wherein steps v)-vii) take place under water; and wherein steps vi)-vii) are repeated until a constant value is obtained, without lifting the probe from the hair.

In this way, we have found that very small differences in friction are picked up, which are consistent with consumer data.

BRIEF DESCRIPTION OF THE FIGURES

Embodiments of the present disclosure will now be described with reference to the following non-limiting drawings in which.

Figure 1:
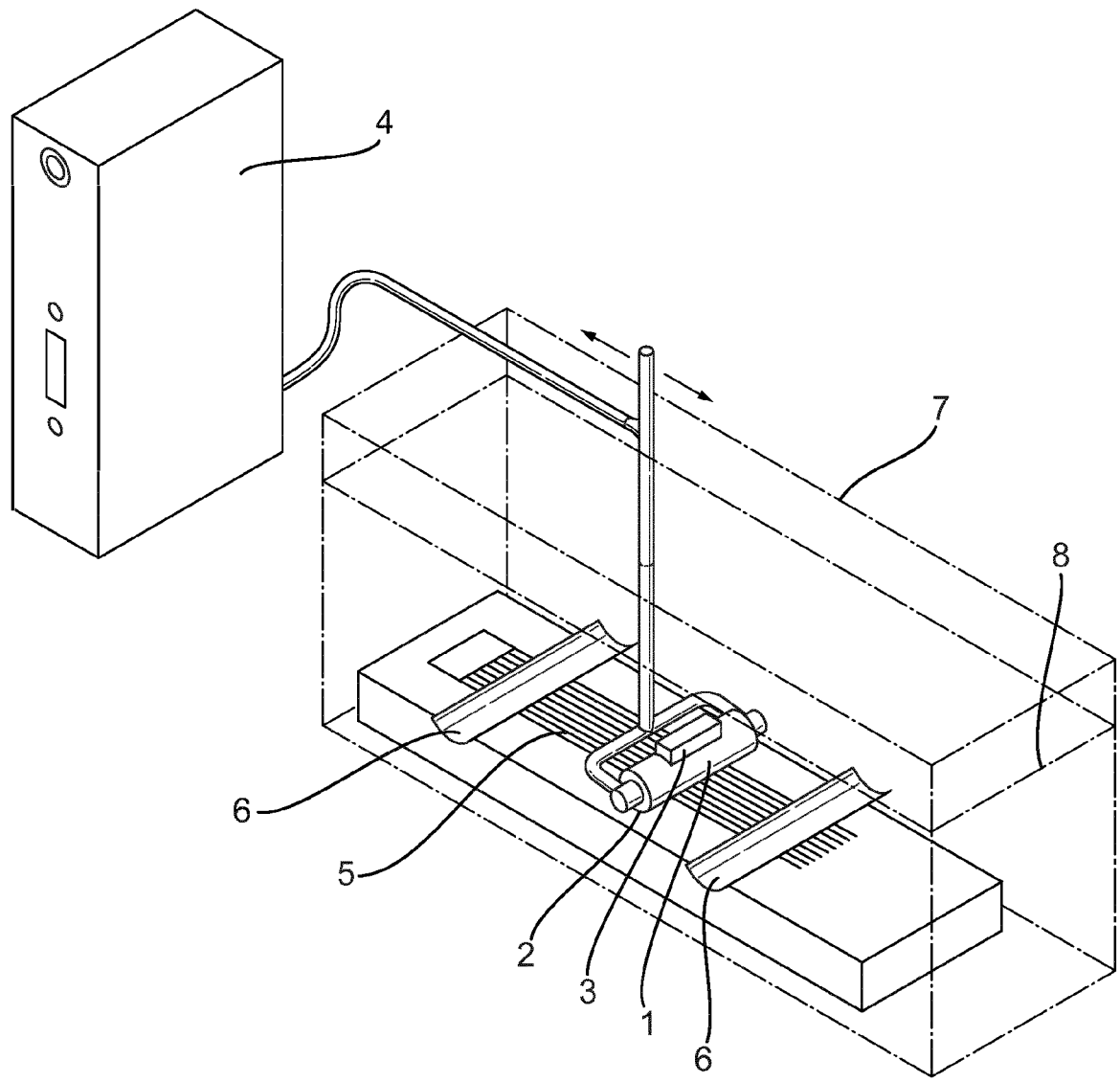
FIG. 1 is a perspective view of the system for use on the method of the present disclosure.

The system in FIG. 1 comprises a friction probe (1) having a contact surface (2) that comprises surfactant, fitted with a weight (3), connected to a Texture Analyser (4); and showing a bundle of hair fibres (5) clamped at two positions along its length with a clamp (6); the clamp and friction probe being positioned in a water bath (7) below the fill line (8).

DETAILED DESCRIPTION

The Method

Preferably, steps vi)-vii) of the method are repeated without lifting the probe from the hair, until a constant value is obtained. Preferably, steps vi)-vii) are repeated from 15 to 100 times, more preferably from 20 to 60 times, most preferably from 30 to 50 times.

Preferably, step iv)-vi) of the method are conducted without opening the security means.

The phrase 'moving the probe along the hair fibres' in Step iv) should be understood to mean that the probe is sliding on the hair fibres from one end to the other end, whilst the probe is sliding, the hair fibre is kept stationary.

The hair fibres are aligned prior to contact with the probe. This is preferably achieved by combing or brushing the hair.

A method of assessing the friction reducing efficacy of a hair treatment composition, comprises the step of treating a bundle of hair fibres with a first hair treatment composition, before carrying out the method of the first aspect of the present disclosure. Herein, 'treating' should be understood to mean applying the hair composition to a bundle of hair fibres. In a preferred embodiment, the hair fibres are cleaned and/or rinsed prior to the application of the hair composition. Preferably, the hair fibres are rinsed after application of the hair composition, but before securing it on the means.

The method may additionally comprise the step of treating a bundle of hair fibres with a second hair treatment composition, carrying out the method of the first aspect of the present disclosure and comparing the friction of hair treated with the first hair treatment composition with the friction of the hair treated with the second hair treatment composition.

The Bundle of Hair Fibres

The bundle of hair fibres is preferably bound or glued at one end. Preferably the bundle of hair fibres is a switch preferably comprising from 50 to 5000 hair fibres, most preferably from 500 to 2000 hair fibres.

Preferably, the hair switches are from 1 to 20 g in weight, more preferably 2 to 10 g. Preferably the switches are from 10 to 50 cm in length, more preferably from 15 to 30 cm in length.

The Friction Probe

The friction probe has a contact surface that contacts the hair during use. The contact surface is preferably the outer surface of the friction probe.

Preferably, the friction probe comprises a rubber material, preferably a synthetic rubber, most preferably Neoprene.

Preferably, the contact surface of the friction probe comprises surfactant Preferably the level of surfactant on the friction probe is from 10 $\mu g/cm^2$ to 1500 $\mu g/cm^2$, more preferably 50 $\mu g/cm^2$ to 1000 $\mu g/cm^2$, even more preferably 80 $\mu g/cm^2$ to 500 $\mu g/cm^2$, most preferably 100 $\mu g/cm^2$ to 200 $\mu g/cm^2$.

The weight of the friction probe itself is approximately from 20 to 100 g, preferably from 40 to 80 g, more preferably 60 g. The friction probe is fitted with a weight in the range of from 10 to 500 g, preferably from 50 to 300 g, most preferably from 100 to 200 g. The weight enables good contact between the probe and the hair.

Preferably, the friction probe is a stainless steel cylinder, coated with said rubber material.

Surfactant may be added to the probe by treating with aqueous surfactant and drying.

A preferred method is, prior to use, the probe is first washed with an aqueous surfactant composition, having a concentration of surfactant of from 5 to 25 wt % by weight of the total aqueous surfactant composition, and rinsed with water. The probe is then soaked in a dilute aqueous surfactant solution of concentration of from 10 ppm to 1500 ppm surfactant, and dried.

The aqueous surfactant composition, has a concentration of from 5 to 25 wt %, preferably 8 to 20 wt %, by weight of the total aqueous surfactant composition, for example, 14 wt %.

Following treatment with the aqueous surfactant composition, the probe is rinsed with water (preferably until no slippery feel remains) before being soaked in dilute aqueous surfactant solution of concentration 10 ppm to 1500 ppm, preferably 50 to 500 pm, most preferably 80 to 200 ppm, for example 140 ppm, preferably for 30 seconds to 5 minutes, more preferably from 1 minute to 3 minutes.

The probe is then dried, preferably for 10 min to 3 hours, most preferably 1.5 to 2.5 hours.

Preferably, the surfactant in both the aqueous surfactant composition and the dilute surfactant solution is an anionic surfactant, preferably Sodium Lauryl Ether Sulphate (SLES).

A preferred probe is first washed with aqueous anionic surfactant composition, having a concentration of from 5 to 25 wt %, and rinsed with water, then soaked in dilute aqueous surfactant solution of concentration of 10 ppm to 1500 ppm for 1 to 3 minutes, and dried for 1.5 to 2.5 hours.

Securing Means

The bundle of hair fibres, is secured with a securing means. Preferably, the securing means is a clamp. Preferably, the hair is secured at two positions along its length.

The Water Bath

The securing means and friction probe are positioned in the water bath below the fill line.

Preferably, the water is warm, preferably between 25 and 40° C.

The Texture Analyser (TA)

Any suitable texture analyser may be used, for example, a TA.XT2i Texture Analyser supplied by Stable Micro Systems, Surrey, UK. The TA picks up the friction from the hair through the probe.

The probe is connected to the Texture Analyser.

Without wishing to be bound by any theory, it is believed that the present disclosure operates in a region between 'boundary lubrication' and 'hydrodynamic lubrication'. The region itself is normally named 'elastohydrohynamic lubrication and mixed lubrication'. In the hydrodynamic lubrication region, the fluid completely isolates the friction surfaces (the probe and the hair), and internal fluid friction alone determines tribological characteristics. In the 'boundary lubrication' region, the hydrodynamic effects of lubricants (for example, the hair composition left on the fibres), do not significantly influence tribological characteristics. By contrast, in the 'mixed lubrication' region, the fluid (such as fluid viscosity), the pressure, the solid surfaces are all influencing factors. The inventors have observed that the system according to claim 1 can be used to differentiate even small difference of friction on hair, resulting from different hair treatment compositions. Further, the difference seems to correlate well with the consumer perception.

The Hair Treatment Composition

Preferred hair treatment compositions for use in the methods of the present disclosure are rinse off compositions.

Preferred hair treatment compositions are selected from a shampoo, a rinse-off hair conditioner and a hair mask.

Rinse off conditioners for use in the present disclosure are conditioners that are typically left on wet hair for 1 to 2 minutes before being rinsed off.

Hair masks for use in the present disclosure are treatments that are typically left on the hair for 3 to 10 minutes, preferably from 3 to 5 minutes, more preferably 4 to 5 minutes, before being rinsed off.

Treatments compositions for use in the method of the present disclosure preferably comprise conditioning agents. Conditioning agents are preferably selected from cationic surfactants, used singly or in admixture.

Cationic surfactants useful in compositions for use in the method of the present disclosure contain amino or quaternary ammonium hydrophilic moieties which are positively charged when dissolved in aqueous composition.

Examples of suitable cationic surfactants are those corresponding to the formula:

$$[N(R_1)(R_2)(R_3)(R_4)]^+(X)^-$$

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present disclosure are monoalkyl quarternary ammonium compounds in which the akyl chain lengthy is $C_{16}$ to $C_{22}$.

Suitable examples of such materials correspond to the formula:

$$[N(R_5)(R_6)(R_7)(R_8)]^+(X)^-$$

in which $R_5$ is a hydrocarbon chain having 16 to 22 carbon atoms or a functionalised hydrocarbyl chain with 16 to 22 carbon atoms and containing ether, ester, amido or amino moieties present as substituents or as linkages in the radical chain, and $R_6$, $R_7$ and $R_8$ are independently selected from (a) hydrocarbyl cahins of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 16 to 22 carbon atoms. They may be derived from source oils which contain substantial amounts of fatty acids having the desired hydrocarbyl chain length.

Typical monoalkyl quarternary ammonium compounds of the above general formula for use in compositions for use in the method of the present disclosure include:
 (i) Cetyl trimethylammonium chloride (available commercially, for example, as Dehyquart ex BASF); behenyl trimethyl ammonium chloride (available, for example, as Incroquat™ Behenyl, ex Croda)
 (ii) Compounds of the formula:

$$[N(R_1)(R_2)((CH_2CH_2O)_xH)((CH_2CH_2O)_yH]^+(X)^-$$

wherein:
 x+y is an integer from 2 to 20;
 $R_1$ is a hydrocarbyl chain having 16 to 22 carbon atoms and containing ether, ester, amido or amino moieties present as substituent's or as linkages in the radical chain;
 $R_2$ is a $C_1$-$C_3$ alkyl group or benzyl group, preferably methyl, and
 X is a salt-forming anion such as those selected from halogen, (e.g. chloride, bromide), acetate, citrate, lactate, glycolate, phosphate nitrate, sulphate, methosulphate and alkylsulphate radicals.
 (iii) Compounds of the formula:

$$[N(R_1)(R_2)(R_3)((CH_2)_nOH)]^+(X)^-$$

wherein:
 n is an integer from 1 to 4, preferably 2;
 $R_1$ is a hydrocarbyl chain having 16 to 22 carbon atoms;
 $R_2$ and $R_3$ are independently selected from $C_1$-$C_3$ alkyl groups, and are preferably methyl, and
 X— is a salt-forming anion such as those selected from halogen, (e.g. chloride, bromide), acetate, citrate, lactate, glycolate, phosphate nitrate, sulphate, alkylsulphate radicals.

Mixtures of any of the foregoing cationic surfactants compounds may also be suitable.

Examples of suitable cationic surfactants for use in hair compositions for use in the method of the present disclosure include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31, Quaternium-98 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2014/016352 and WO2014/016351. A preferred hair conditioning composition of this type comprises from 0.4 to 8% wt. fatty alcohol having from 8-22 carbons, from 0.1 to 2 wt % cationic surfactant component, water, and wherein the composition confers a Draw Mass of from 1 to 250 g to hair treated with the conditioning composition. Draw Mass is the mass required to draw a hair switch through a comb or brush.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present disclosure may comprise a miscellar structured liquid.

The pH of a conditioner comprising the present composition is preferably 3-5. More preferably the pH of the composition is 4.5-5.5.

Where the composition has a pH of less than 3.10 it is preferred that it is in the form of a conditioning mask for intense treatment.

Further conditioning ingredients include conditioning oils, preferably selected from coconut oil and olive oil.

The present disclosure will now be illustrated by the following non-limiting Examples:

Example 1: Composition for Treatment of Hair Prior to Friction Analysis

A hair conditioner composition was prepared and used to treat hair prior to friction analysis using the method of the present disclosure. The composition is given in Table 1.

TABLE 1

Compositions of Conditioner A

| INCI | Active Level | A |
|---|---|---|
| Stearamidopropyl dimethylamine | 100 | 1 |
| Behentrimonium Chloride | 70 | 1 |
| Cetearyl Alcohol | 100 | 4 |
| Preservative | 55 | 0.1 |
| Sodium Chloride | 100 | 0.1 |
| Perfume | 100 | 0.6 |
| Preservative | 100 | 0.04 |
| Water | 100 | To 100 |

Formulation A was made by adding the cationic surfactants to the fatty alcohol and stirring at 85° C. Gradually this mixture was added to water, typically at 55° C., such that the mixture temperature was 60° C. This temperature was maintained for 30 minutes with stirring. The mixture was then cooled towards ambient by adding more water, and other ambient temperature ingredients, and by the use of external cooling if required, and stirred.

Example 2: Treatment of Hair with Composition A Prior to TA Friction Measurements in Accordance with the Present Disclosure The hair used was dark brown European hair, in switches of 5 g weight and 6 inch length.

The hair was treated with Composition A as follows:—
Hair was first treated with a cleansing shampoo using the following method:—

The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 1 minute.

The wet hair was then treated with Conditioner A using the following method:—

Conditioner was applied to the wet hair at a dose of 0.2 ml of conditioner per 1 g of hair and massaged into the hair for 1 minute. The hair was rinsed under running water for 1 minute and excess water removed.

Example 3: Friction Measurement of Hair Treated with Composition A

Friction was measured using the apparatus and method of the present disclosure as follows:

Friction was measured using a TA. XT2i Texture Analyser supplied by Stable Micro Systems, Surrey, UK. The friction probe was a stainless steel cylinder, which was coated with rubber material. The load on the friction contact was approximately 138 g. When in use, an area of contact between the outer surface of the friction probe and the hair of approximately 1.0 cm$^2$ was achieved.

Surfactant was added to the probe as follows:

The probe was first washed with an aqueous composition of Sodium Lauryl Ether Sulphate (SLES) at a concentration of 14 wt %, by weight of the total aqueous surfactant composition, and rinsed with water. The probe was then soaked in a dilute solution of SLES having a concentration of 14 ppm, for 2 minutes, and then dried for 2 hours.

The methodology used to assess the friction properties of haft treated with Conditioner A was as follows:

A switch of hair was securely mounted onto the texture analyser, the hair fibres being aligned by combing before being secured in a flat configuration. The haft was immersed in the water bath. The friction probe was placed onto the haft and moved along the hair at a speed of 10 mms$^{-1}$ to measure the friction between the probe and the hair. The measurement was repeated 30 times.

The friction values reported below are of friction hysteresis in units of g·mm, obtained by integrating the total measured friction force over the total distance travelled by the probe, with and against cuticle.

Figure 2:
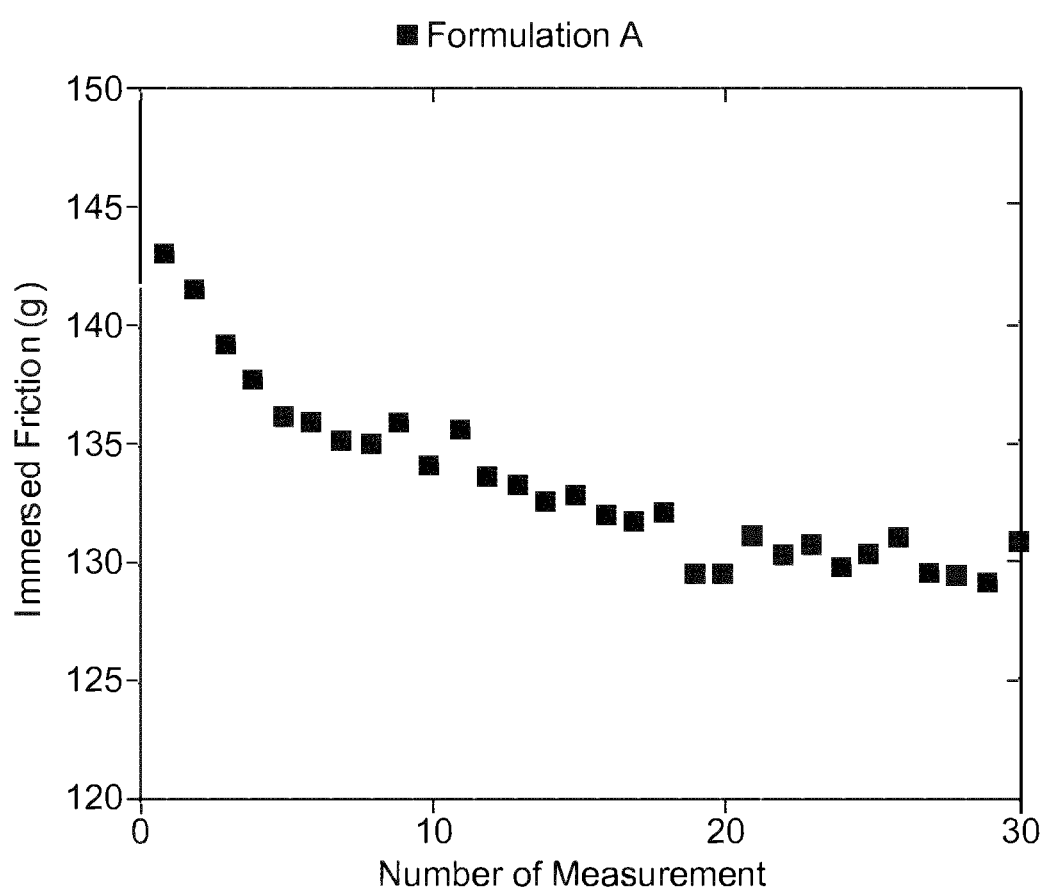
FIG. 2 shows an immersed fiction profile for treated hair using the method of the present disclosure.

Immersed friction measured, and repeated 30 times, on hair switches treated with Conditioner A are given in the Table 2, and shown graphically in FIG. 2.

TABLE 2 immersed fiction measurements for hair treated with Conditioner A, for 1 to 30 repeats

| Measurement number | Formulation A |
|---|---|
| 1 | 142.88 |
| 2 | 141.41 |
| 3 | 139.14 |
| 4 | 137.54 |
| 5 | 136.07 |
| 6 | 135.78 |
| 7 | 134.99 |
| 8 | 134.89 |
| 9 | 135.8 |
| 10 | 133.95 |
| 11 | 135.54 |
| 12 | 133.55 |
| 13 | 133.14 |
| 14 | 132.45 |

TABLE 2-continued immersed fiction measurements for hair treated
with Conditioner A, for 1 to 30 repeats

| Measurement number | Formulation A |
|---|---|
| 15 | 132.65 |
| 16 | 131.86 |
| 17 | 131.6 |
| 18 | 131.98 |
| 19 | 129.42 |
| 20 | 129.46 |
| 21 | 131.11 |
| 22 | 130.25 |
| 23 | 130.71 |
| 24 | 129.67 |
| 25 | 130.23 |
| 26 | 130.91 |
| 27 | 129.4 |
| 28 | 129.35 |
| 29 | 128.99 |
| 30 | 130.76 |

The data in Table 2 is presented graphically in FIG. 2.

FIG. 2 shows the immersed fiction profile for hair treated with Conditioner A, repeated 30 times.

It will seen that the friction levels out at a true constant value, only after several measurements, which is much more accurate and useful for comparative purposes than friction measurements that are not repeated until constant.

Example 4: Friction Measurement by Probe Fitted with Different Weights

Composition A was used to treat the hair fibres as described in Example 1. All probes comprise surfactant prior to use. All other experimental details are as described in Example 3 except that the probe is fitted with weights of 0 g (no weight), 138 g and 1000 g respectively.

After 30 measurements, the average friction recorded for probe fitted with 138 g weight is 133.18 g mm, in good agreement with the data obtained in Table 2. The average friction recorded for probe fitted with 1000 g weight is found artificially increased to 216.22 g mm. Moreover, this high friction caused difficulty in repeating the measurements because hair constantly slipped from clamp, then floated on water. On the other hand, no weight on probe has significantly decreased the friction. No meaningful data could be recorded.

What is claimed is:

1. A method of measuring a wet friction of a bundle of hair, using a system comprising:
    i) a friction probe, having a contact surface, the probe fitted with a weight in the range of from 10 g to 500 g, inclusive;
    ii) a means for securing the bundle of hair; and
    iii) a water bath;
    wherein the friction probe is connected to a texture analyser, the method comprising the steps of:
    i) providing a bundle of hair fibres;
    ii) aligning the bundle of hair fibres;
    iii) securing the bundle of hair fibres;
    iv) immersing the bundle of hair fibres under water in the water bath;
    v) contacting the bundle of hair fibres with the contact surface of the friction probe, which is fitted with the weight;
    vi) moving the probe along the hair fibres; and
    vii) recording the friction generated under step vi);
    wherein steps v)-vii) take place under water; and
    wherein steps vi)-vii) are repeated until a constant value is obtained, without lifting the probe from the bundle of hair fibres.

2. The method of claim 1, further comprising the step of treating the bundle of hair fibres with a first hair treatment composition.

3. The method of claim 2, further comprising the steps of:
    treating the bundle of hair fibres with a second hair treatment composition; and
    comparing the friction of the bundle of hair fibres treated with the first hair treatment composition with the friction of the bundle of hair fibres treated with the second hair treatment composition.

4. The method of claim 1, wherein steps vi) to vii) are repeated from 15 to 100 times.

5. The method of claim 1, wherein the probe comprises surfactant.

6. The method of claim 5, wherein a level of the surfactant on the friction probe is from 10 μg/cm$^2$ to 1500 μg/cm$^2$, inclusive.

7. The method of claim 1, wherein the friction probe comprises a rubber material.

\* \* \* \* \*